United States Patent [19]

Holmwood et al.

[11] Patent Number: 4,868,196

[45] Date of Patent: * Sep. 19, 1989

[54] ETHER DERIVATIVES OF SUBSTITUTED 1-HYDROXYALKYL- AZOLES AS FUNGICIDES AND PLANT GROWTH REGULATORS

[75] Inventors: Graham Holmwood; Erik Regel, both of Wuppertal; Gerhard Jäger, Leverkusen; Karl H. Büchel, Burscheid; Paul-Ernst Frohberger, Leverkusen; Wilhelm Brandes, Leichlingen; Klaus Lürssen, Bergisch-Gladbach, all of Fed. Rep. of Germany

[73] Assignee: Bayer Aktiengesellschaft, Leverkusen, Fed. Rep. of Germany

[*] Notice: The portion of the term of this patent subsequent to Feb. 9, 2005 has been disclaimed.

[21] Appl. No.: 859,276

[22] Filed: May 2, 1986

Related U.S. Application Data

Continuation-in-part of Ser. No. 458,087 Jan. 14, 1983.

[30] Foreign Application Priority Data

Jan. 27, 1982 [DE] Fed. Rep. of Germany ....... 3202604

[51] Int. Cl.$^4$ .................. A01N 43/653; C07D 249/12
[52] U.S. Cl. .................... 514/383; 514/184; 548/262; 548/341
[58] Field of Search ............... 548/262, 101; 514/383, 514/184

[56] References Cited

U.S. PATENT DOCUMENTS

| | | | |
|---|---|---|---|
| 4,085,209 | 4/1978 | Miller et al. | 514/399 |
| 4,123,542 | 10/1978 | Walker | 548/262 |
| 4,233,311 | 11/1980 | Kramer et al. | 514/383 |
| 4,243,405 | 1/1981 | Balasubramanyan et al. | 71/76 |
| 4,277,475 | 7/1981 | Vickery | 548/262 |
| 4,507,140 | 3/1985 | Sugavanam | 548/262 |
| 4,723,984 | 2/1988 | Holmwood et al. | 71/76 |

FOREIGN PATENT DOCUMENTS 3018866 11/1981 Fed. Rep. of Germany ...... 548/262

Primary Examiner—Richard L. Raymond
Assistant Examiner—Patricia L. Morris
Attorney, Agent, or Firm—Sprung Horn Kramer & Woods

[57] ABSTRACT

Compounds which are ether derivatives of substituted 1-hydroxyalkyl-azoles, of the general formula

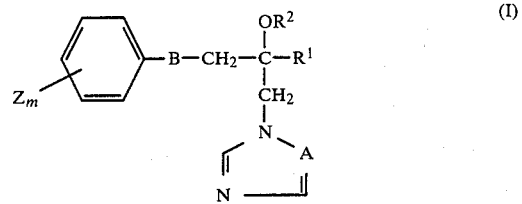

in which
  A represents a nitrogen atom or a CH group,
  B represents oxygen, sulphur or a CH$_2$ group,
  R$^1$ represents a substituted alkyl, optionally substituted cycloalkyl or optionally substituted phenyl radical or, if either A represents a nitrogen atom, or if A represents the CH group and at the same B represents oxygen or sulphur, R$^1$ also represents an unsubstituted alkyl radical,
  R$^2$ represents an alkyl, alkenyl, alkinyl, optionally substituted phenyl or optionally substituted benzyl radical,
  Z represents a halogen atom or an alkyl, cycloalkyl, alkoxy, alkylthio, halogenoalkyl, halogenoalkoxy, halogenoalkylthio, optionally substituted phenoxy, optionally substituted phenylalkyl or optionally substituted phenylalkoxy radical and
  m is 0, 1, 2 or 3, and acid addition salts and metal salt complexes thereof, are novel, are prepared as described, and find use as fungicides and as agents for regulating plant growth.

7 Claims, No Drawings

ETHER DERIVATIVES OF SUBSTITUTED 1-HYDROXYALKYL- AZOLES AS FUNGICIDES AND PLANT GROWTH REGULATORS

This is a division of application Ser. No. 458,087, filed Jan. 14, 1983, now pending.

The present invention relates to certain new ether derivatives of substituted 1-hydroxyalkyl-azoles, to a process for their production and to their use as fungicides and plant growth regulators.

It has already been disclosed that certain biphenylyl-hydroxyalkyl-azole derivatives, such as 2-(4-biphenylyl)-1-(2,4-dichlorophenyl)- and -phenyl-3-(1,2,4-triazol-1-yl)-2-propanol and 4-biphenylyl-2-chloro- and -fluoro-phenyl-(1,2,4-triazol-1-yl-methyl)-carbinol, have good fungicidal properties and, when applied in particular amounts, also good plant growth-regulating properties (see U.S. Ser. No. 144,102, filed Apr. 28, 1980, now abandoned.) However, the activity of these compounds is not always completely satisfactory, especially when low amounts and concentrations are applied. In addition, the patent literature discloses ether derivatives of certain hydroxyalkylimidazoles (see U.S. patent specification Nos. 4,123,542 and 4,277,475) which have an action against fungi which are pathogenic to humans, and which can be used as medicaments and also as contraceptives (U.S. patent specification No. 4,277,475).

Furthermore, it has already been disclosed that certain phenyl-triazolyl-ethanol derivatives, such as 1-(4-chlorophenyl)-2-(1,2,4-triazol-1-yl)-1-ethanol, have fungicidal properties (see U.S. Ser. No. 291,700, filed Aug. 10, 1981, now U.S. Pat. No. 4,776,877.) The action of these compounds is also not always satisfactory, especially when low amounts and concentrations are applied.

The present invention now provides, as new compounds, the ether derivatives of substituted 1-hydroxyalkylazoles, of the general formula

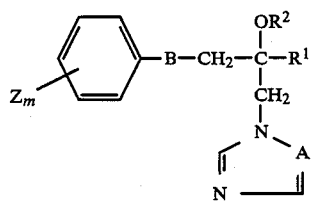

in which
A represents a nitrogen atom or a CH group,
B represents oxygen, sulphur or a $CH_2$ group,
$R^1$ represents a substituted alkyl, optionally substituted cycloalkyl or optionally substituted phenyl radical, or, if either A represents a nitrogen atom, or A represents the CH group and at the same time B represents oxygen or sulphur,
$R^1$ also represents an unsubstituted alkyl radical,
$R^2$ represents an alkyl, alkenyl, alkinyl, optionally substituted phenyl or optionally substituted benzyl radical,
Z represents a halogen atom or an alkyl, cycloalkyl, alkoxy, alkylthio, halogenoalkyl, halogenoalkoxy, halogenoalkylthio, optionally substituted phenoxy, optionally substituted phenylalkyl or optionally substituted phenylalkoxy radical and
m is 0, 1, 2 or 3,
and acid addition salts and metal salt complexes thereof.

The compounds of the formula (I) possess an asymmetric carbon atom and can therefore be obtained in the two optical isomer forms.

The present invention further provides a process for the production of a compound of the present invention, characterized in that an alcoholate of a 1-hydroxyalkylazole, of the general formula

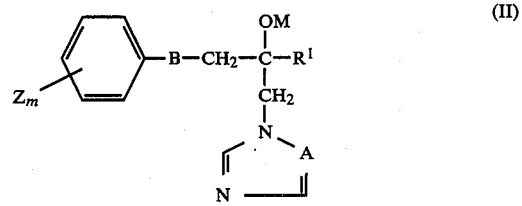

in which
A, B, $R^1$, Z and m have the abovementioned meanings and
M represents an alkali metal or a quaternary ammonium or phosphonium group,
is reacted with a halide of the general formula $$R^2—Hal \qquad (III)$$

in which
$R^2$ has the abovementioned meaning and
Hal represents a halogen atom,
in the presence of a diluent, and, if desired, an acid or a metal salt is then added onto the compound of the formula (I) thus obtained.

It has also been found that the new ether derivatives of substituted 1-hydroxyalkyl-azoles of the formula (I) have powerful fungicidal and powerful plant growth-regulating properties.

Surprisingly, the ether derivatives of the formula (I) according to the invention have better fungicidal and better plant growth-regulating actions than the abovementioned triazolyl derivatives known from the state of the art. The active compounds according to the invention thus represent an enrichment of the art.

Preferred compounds of the present invention are those
in which
$R^1$ represents a grouping of the general formula

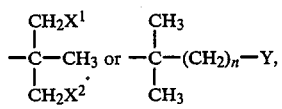

a cycloalkyl radical which has 3 to 7 carbon atoms and is optionally substituted by alkyl with 1 or 2 carbon atoms, or an optionally substituted phenyl radical (preferred substituents which may be mentioned being: halogen, alkyl with 1 to 4 carbon atoms and halogenoalkyl with 1 or 2 carbon atoms and 1 to 5 identical or different halogen atoms, such as, preferably, fluorine and chlorine atoms);
$X^1$ represents a hydrogen or halogen atom;
$X^2$ represents a halogen atom;
Y represents an alkyl, alkoxy, alkylthio, halogenoalkoxy, halogenoalkylthio, alkenyl with 2 to 6 carbon atoms, alkoxycarbonyl with 1 to 4 carbon atoms in the alkyl part or cyano radical or an optionally substituted radical selected from phenyl, phenoxy, phenylthio, phenylalkoxy with 1 to 4 carbon atoms in the alkyl part and phenylalkylthio with 1 to 4 carbon atoms in the alkyl part (preferred substituents on the phenyl which may be mentioned in each case being: halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, such as, in particular, fluorine and chlorine atoms, cyclohexyl, dialkylamino with 1 to 4 carbon atoms in each alkyl part, nitro, cyano and alkoxycarbonyl with 1 to 4 carbon atoms in the alkyl part);

n is 0, 1 or 2;

Z represents a halogen atom, an alkyl radical with 1 to 4 carbon atoms, a cycloalkyl radical with 5 to 7 carbon atoms, an alkoxy or alkylthio radical with in each case 1 to 4 carbon atoms, a halogenoalkyl, halogenoalkoxy or halogenoalkylthio radical with in each case 1 or 2 carbon atoms and 1 to 5 identical or different halogen atoms, such as, in particular, fluorine and chlorine atoms, or a phenyl phenoxy, or phenylalkyl or phenylalkoxy radical, with 1 or 2 carbon atoms in the alkyl part or in the alkoxy part, each of which is optionally substituted by halogen or alkyl with 1 or 2 carbon atoms;

$R^2$ represents a straight-chain or branched alkyl radical with 1 to 4 carbon atoms, a straight-chain or branched alkenyl or alkinyl radical with in each case 2 to 4 carbon atoms or an optionally substituted phenyl or benzyl radical, preferred substituents on the phenyl being those phenyl substituents which have already been mentioned in the case of Y; and A, B and m have the abovementioned meanings.
Preferred compounds of the present invention are also those
in which
$R^1$ represents a straight-chain or branched alkyl radical with 1 to 4 carbon atoms;
A represents a nitrogen atom;
$R^2$ and Z have meanings given immediately above for the other preferred compounds of the invention; and B and m have the abovementioned meanings. Preferred compounds of the present invention are, moreover, those
in which
$R^1$ represents a straight-chain or branched alkyl radical with 1 to 4 carbon atoms;
A represents the CH group;
B represents oxygen or sulphur;
$R^2$ and Z have the meanings given immediately above for other preferred compounds of the invention; and
m has the abovementioned meaning. Particularly preferred compounds of the present invention are those in which
$R^1$ represents a grouping of the general formula

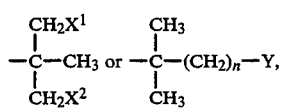

a cyclopropyl, cyclopentyl or cyclohexyl radical each of which is optionally substituted by methyl or ethyl, or a phenyl radical which is optionally mono-, di- or trisubstituted by fluorine, chlorine, methyl or trifluoromethyl;

$X^1$ represents a hydrogen, fluorine, chlorine or bromine atom;

$X^2$ represents a fluorine, chlorine or bromine atom;

Y represents a methyl, ethyl, propyl, methoxy, ethoxy, methylthio, ethylthio, trifluoromethoxy, trifluoromethylthio, vinyl, methoxycarbonyl, ethoxycarbonyl or cyano radical or an optionally mono-, di- or tri-substituted phenyl, phenoxy, phenylthio, phenylmethoxy or phenylmethylthio radical (substituents on the phenyl which may be mentioned being, in each case: fluorine, chlorine, methyl, ethyl, methoxy, methylthio, trifluoromethyl, trifluoromethoxy, trifluoromethylthio, dimethylamino, methoxycarbonyl and ethoxycarbonyl);

n is 0, 1 or 2;

Z represents a fluorine, chlorine or bromine atom, a methyl, tert.-butyl, cyclohexyl, methoxy, methylthio, trifluoromethyl, trifluoromethoxy or trifluoromethylthio radical, or a phenyl, phenoxy, benzyl or benzyloxy radical which is optionally mono-, di- or tri-substituted by fluorine, chlorine or methyl;

$R^2$ represents a methyl, ethyl, n-propyl, isopropyl, n-butyl, isobutyl, allyl or propargyl radical or an optionally mono-, di- or tri-substituted phenyl or benzyl radical, phenyl substituents thereon which may be mentioned being: fluorine, chlorine, methyl, ethyl, methoxy, methylthio, trifluoromethyl, trifluoromethoxy and trifluoromethylthio; and A, B and m have the abovementioned meanings.
Particularly preferred compounds of the present invention are also those
in which
$R^1$ represents a tert.-butyl, isopropyl or methyl radical;
A represents a nitrogen atom;
$R^2$ and Z have the meanings given immediately above for the other particularly preferred compounds of the invention; and
B and m have the abovementioned meanings.
Particularly preferred compounds of the present invention are, moreover, those
in which
$R^1$ represents a tert.-butyl, isopropyl or methyl radical;
A represents a CH group;
B represents oxygen or sulphur;
$R^2$ and Z have the meanings given immediately above for other particularly preferred compounds of the invention; and m has the abovementioned meaning.

Preferred and particularly preferred compounds according to the invention, of course, include addition products of acids with those ether derivatives of substituted 1-hydroxyalkyl-azoles of the formula (I) in which the substituents A, B, $R^1$, $R^2$ and $Z_m$ have the meanings which have already been mentioned for preferred and particularly preferred compounds of the invention.

Preferred acids which can be added include hydrogen halide acids (such as hydrobromic acid, and especially, hydrochloric acid), phosphoric acid, nitric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

Preferred compounds according to the invention also include the addition products of salts of metals of main groups II to IV and sub-groups I and II and IV to VIII with ether derivatives of substituted 1-hydroxyalkylazoles of the formula (I) in which the substituents A, B, $R^1$, $R^2$ and $Z_m$ have the meanings which have already been mentioned for preferred and particularly preferred compounds of the invention.

Salts of copper, zinc, manganese, magnesium, tin iron and nickel are particularly preferred in this context. Possible anions of these salts are those which are derived from acids which lead to physiologically acceptable addition products. In this connection, particularly preferred acids of this type are the hydrogen halide acids (such as hydrochloric acid and hydrobromic acid) and furthermore phosphoric acid, nitric acid and sulphuric acid.

If, for example, the sodium alkanolate of 2-(4-chlorophenoxymethyl)-3,3-dimethyl-1-(1,2,4-triazol-1-yl)-butan-2-ol and iodomethane are used as starting substances, the course of the process according to the invention can be represented by the following equation:

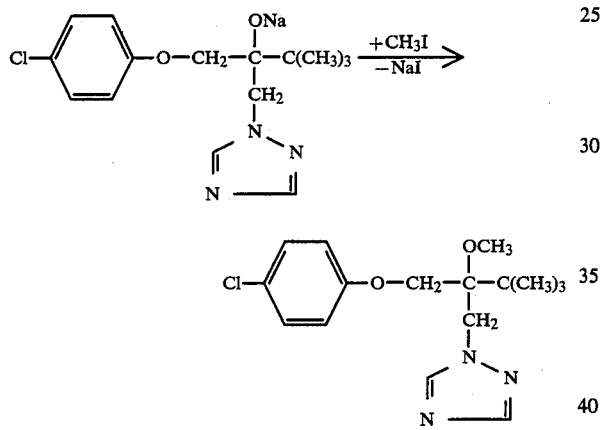

Preferred alcoholates of 1-hydroxyalkylazoles, of formula (II), to be used as starting substances in carrying out the process according to the invention are those in which A, B, $R^1$, Z and m have the meanings which have already been respectively mentioned in connection with the description of the preferred and particularly preferred compounds according to the invention and M represents the alkali metals lithium, sodium or potassium or represents the following quaternary ammonium groups: tetrabutylammonium, N-benzyl-N,N,N-trimethylammonium, hexadecyltrimethylammonium, tetraethylammonium, tetramethylammonium, methyl-trioctylammonium, N-phenyl-N,N,N-trimethylammonium, N-(4-methylbenzyl)-N,N,N-trimethylammonium, N-benzyl-N,N-dimethyl-N-dodecylammonium, N,N-dibenzyl-N,N-dimethylammonium, benzyldimethyl-n-hexadecylammonium, benzyltributylammonium, benzyltriethyl-ammonium, butyl-tripropylammonium, octadecyltrimethylammonium, tetrahexylammonium, tetraoctylammonium and hexadecylpyridinium; or represents the following phosphonium groups: tertraphenylphosphonium, hexadecyltributylphosphonium, ethyl-triphenylphosphonium or methyl-triphenylphosphonium.

The alcoholates of the formula (II) are not yet known. However, they can be obtained in a generally known manner by reacting the corresponding substituted 1-hydroxyalkyl-azole of the general formula

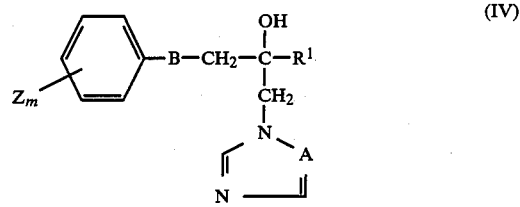

in which

A, B, $R^1$, Z and m have the abovementioned meanings, with suitable strong base (such as an alkali metal amide or hydride or a quaternary ammonium hydroxide or phosphonium hydroxide) in an inert solvent (such as dioxane) at room temperature.

Some of the substituted 1-hydroxyalkyl-azoles of the formula (IV) are known (see DE-OS (German Published Specification) No. 3,018,866), and some of them are the subject of an, as yet unpublished, copending patent application. They are obtained by reacting an oxirane of the general formula

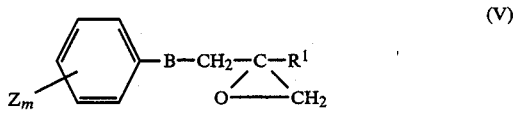

in which

B, $R^1$, Z and m have the abovementioned meanings, with an azole of the general formula

in which

A has the abovementioned meaning, in the presence of an inert organic solvent (such as ethanol) and, if appropriate, in the presence of a base (such as sodium ethylate), if appropriate under a pressure of 1 to 24 bars, at a temperature between 60° and 150° C., or reacting an azolylmethyl-oxirane of the general formula

in which

A and $R^1$ have the abovementioned meanings, with a (thio)phenol of the general formula

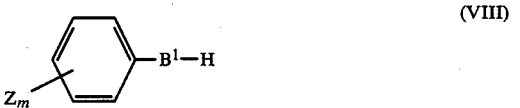

in which

Z and m have the abovementioned meanings and $B^1$ represents oxygen or sulphur,
in the presence of an inert organic solvent (such as ethanol) and, if appropriate, in the presence of a base (such as sodium ethylate), if appropriate under a pressure of 1 to 25 bars, at a temperature between 60° and 100° C.

Some of the oxiranes of the formula (V) are known (see DE-OS (German Published Specification) 3,018,866, and some are the subject of an, as yet unpublished copending patent application. They are obtained by reacting a ketone of the general formula

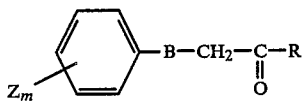 (IX)

in which

B, R, Z and m have the abovementioned meanings, either (α) with dimethyloxosulphonium methylide of the formula

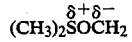 (X)

in a manner which is in itself known, in the presence of a diluent (such as dimethylsulphoxide) at a temperature between 20° and 80° C. (in this context, compare also the statements in J. Am. Chem. Soc. 87, 1363–1364 (1965)), or (β) with trimethylsulphonium methyl-sulphate of the formula

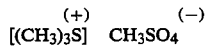 (XI)

in a manner which is in itself known, in the presence of an inert organic solvent (such as acetonitrile) and in the presence of a base (such as sodium methylate) at a temperature between 0° and 60° C., preferably at room temperature (compare also the statements in Heterocycles 8, 397, (1977)).

If appropriate, the oxiranes of the formula (V) thus obtained can be further reacted directly, without being isolated.

The ketones of the formula (IX) required as starting substances in the preparation of the oxiranes of the formula (V) are known (see, for example U.S. Pat. Nos. 3,912,752; 4,147,791; 4,255,434; 4,154,842; 4,284,639; U.S. Ser. No. 307,838, filed Oct. 2, 1981, pending; U.S. Ser. No. 321,642, filed Nov. 16, 1981, pending; German Published Specifications 2,632,602; 2,635,664; and 2,737,489) or they are the subject of as yet unpublished, copending patent applications corresponding to pending U.S. patent Applications, Ser. Nos. 265,050, filed May 19, 1981; 370,754, filed Apr. 22, 1982; 335,942, filed Dec. 30, 1981, or they can be prepared by processes which are known in principle.

The dimethyloxosulphonium methylide of the formula (X) required in process variant (α) is also known (see J. Am. Chem. Soc. 87, 1363–1364 (1965)). It is used in the freshly prepared state in the above reaction, by being produced in situ by reaction of trimethylsulphoxosulphonium iodide with sodium hydride or sodium amide in the presence of a diluent.

The trimethylsulphonium methyl-sulphate of the formula (XI) required in process variant (β) is also known (see Heterocycles 8, 397 (1977)). It is also used in the freshly prepared state in the above reaction, by being produced in situ by reaction of dimethyl sulphide with dimethyl sulphate.

The azolylmethyloxiranes the formula (VII) also to be used as starting substances for the preparation of the 1-hydroxyalkyl-azoles of the formula (IV) are not yet known. However, some of them are the subject of as yet unpublished, copending patent application corresponding to pending U.S. Application, Ser. No. 352,689, filed Feb. 26, 1982, and some of them are the subject of another copending, as yet unpublished patent application or they can be obtained in a generally known manner by epoxidising azolo-ketones of the formula

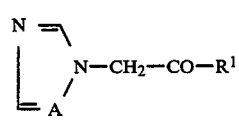 (XII)

in which

A and $R^1$ have the abovementioned meaning, in a manner corresponding to the abovementioned process variants (α) and (β).

The azolo-ketones of the formula (XII) are known (see U.S. Ser. No. 291,700, supra,) DE-OS (German Published Specification) 2,638,470 and U.S. Pat. No. 4,344,953; or they are the subject of as yet unpublished, copending patent application corresponding to pending U.S. patent application Ser. No. 328,871, filed Dec. 8, 1981, or they can be prepared by processes which are known in principle.

The azoles of the formula (VI) and (thio)phenols of the formula (VII) also to be used as starting substances for the preparation of the 1-hydroxyalkyl-azoles of the formula (IV) are generally known compounds of organic chemistry.

Preferred halides of formula (III) also to be used as starting substances for the process according to the invention are those in which $R^2$ has the meanings which have already been mentioned for this substituent in connection with the description of the preferred and particularly preferred compounds according to the invention, and Hal represents a chlorine, bromine or iodine atom.

The halides of the formula (III) are generally known compounds of organic chemistry.

The compounds which follow of the general formula

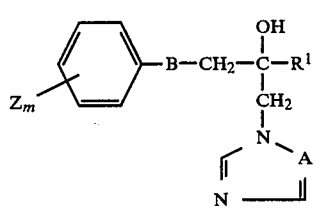 (IV)

(A represents either a nitrogen atom or the CH group) may be mentioned as examples of the substituted 1-hydroxyalkylazoles of the formula (IX) on which the alcoholates of the formula (II) to be used according to the invention as starting substances are based:

TABLE 1

| $Z_m$ | B | $R^1$ |
|---|---|---|
| 4-Cl | O | $C(CH_3)_3$ |
| 4-Cl | $CH_2$ | $C(CH_3)_3$ |
| 4-Cl,2-$CH_3$ | O | $C(CH_3)_3$ |
| 2,4-$Cl_2$ | O | $C(CH_3)_3$ |
| 4-$CH_3$ | O | $C(CH_3)_3$ |
| 2-$CH_3$ | O | $C(CH_3)_3$ |
| 4-F | $CH_2$ | $C(CH_3)_3$ |
| 4-Cl | O |  |
| 4- | O | $C(CH_3)_3$ |
| 2-Cl | O | $C(CH_3)_3$ |
| 2,4-$Cl_2$ | $CH_2$ | $C(CH_3)_3$ |
| 2-$CH_3$ | $CH_2$ | $C(CH_3)_3$ |
| 4-Cl | O | 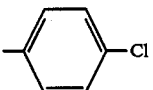 |
| 4-F | O | $C(CH_3)_3$ |
| 3-Cl | O | $C(CH_3)_3$ |
| 2-Cl,4-F | O | $C(CH_3)_3$ |
| 3,4-$Cl_2$ | O | $C(CH_3)_3$ |
| 4-$CH_3$ | $CH_2$ | $C(CH_3)_3$ |
| 4-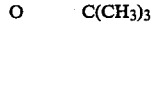 | O | $C(CH_3)_3$ |
| — | O | $C(CH_3)_3$ |
| 4-$OCH_3$ | O | $C(CH_3)_3$ |
| 4-$C(CH_3)_3$ | O | $C(CH_3)_3$ |
| 4-$OCF_3$ | O | $C(CH_3)_3$ |
| 4-F | O | $-C(CH_3)_2CH_2F$ |
| 4-Cl | O | $-C(CH_3)_2CH_2OCH_3$ |
| 4-Cl | S | $C(CH_3)_3$ |
| 4- | O | $-C(CH_3)_2CH=CH_2$ |
| 4-$CH_3$ | O | $-C(CH_3)_3CH_2F$ |
| 4-Cl | O | $-C(CH_3)_2CH_2F$ |
| 4-Cl,2-$CH_3$ | O | $-C(CH_3)_2CH_2F$ |
| 2,4-$Cl_2$ | O | $-C(CH_3)_2CH_2F$ |
| 4-Cl | S | $-C(CH_3)_2CH_2F$ |
| 2-Cl | S | $-C(CH_3)_2CH_2F$ |
| 3,4-$Cl_2$ | S | $-C(CH_3)_2CH_2F$ |
| 4-Cl | O | $-C(CH_2F)_2CH_3$ |
| 2,4-$Cl_2$ | O | $-C(CH_2F)_2CH_3$ |
| 4-Cl,2-$CH_3$ | O | $-C(CH_2F)_2CH_3$ |
| 2,4-$Cl_2$ | O | $-C(CH_3)_2CH_2OCH_3$ |
| 4-Cl, 2-$CH_3$ | O | $-C(CH_3)_2OCH_3$ |
| 4-Cl | O | $-C(CH_3)_2CH_2OC_2H_5$ |
| 4-Cl | O | 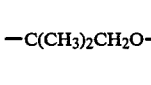 |
| 4-F | O | $-C(CH_3)_2CH_2OCH_3$ |
| 2,4-$Cl_2$ | O | 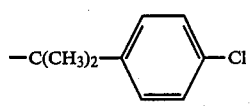 |
| 4-Cl | O | $-C(CH_3)_2CH=CH_2$ |
| 2,4-$Cl_2$ | O | $-C(CH_3)_2CH=CH_2$ |
| 4-F | O | $-C(CH_3)_2CH-CH_2$ |
| 4-Cl | $CH_2$ | $-C(CH_3)_2CH_2F$ |
| 2,4-$Cl_2$ | $CH_2$ | $-C(CH_3)_2CH_2F$ |
| 2,4-$Cl_2$ | $CH_2$ | $-C(CH_2F)_2CH_3$ |
| 4-Cl | $CH_2$ | $-C(CH_2F)_2CH_3$ |
| 4-Cl | $CH_2$ | 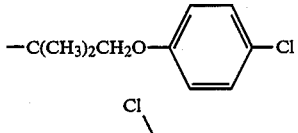 |
| 4-Cl | $CH_2$ | (structure shown) |
| 3,4-$Cl_2$ | S | $-C(CH_3)_3$ |

Possible diluents for the reaction according to the invention are inert organic solvents. These include, as preferences, ethers (such as diethyl ether or dioxane), aromatic hydrocarbons (such as benzene); in individual cases also chlorinated hydrocarbons (such as chloroform, methylene chloride or carbon tetrachloride), and hexamethylphosphoric acid triamide.

The reaction temperatures can be varied within a substantial range in carrying out the process according to the invention. In general, the reaction is carried out at a temperature between 0° and 120° C., preferably between 20° and 100° C.

In carrying out the process according to the invention, 1 to 2 mols of halide of the formula (III) are preferably employed per mol of the alcoholate of the formula (II). To isolate the end products, the reaction mixture is freed from the solvent, and water and an organic solvent are added to the residue. The organic phase is separated off and is worked up and purified in the customary manner.

In a preferred embodiment, a procedure is advantageously followed in which a substituted 1-hydroxyalkylazole derivative of the formula (IV) is used as the starting material and is converted into the alkali metal alcoholate of the formula (II) in a suitable organic solvent by means of an alkali metal hydride or alkali metal amide, and then alcoholate is reacted immediately with a halide of the formula (III), without being isolated, the compounds of the formula (I) according to the invention being obtained in one operation, with elimination of an alkali metal halide.

According to a further preferred embodiment, the preparation of the alcoholates of the formula (II) and the reaction according to the invention are advantageously carried out in a two-phase system (such as aqueous sodium hydroxide solution or potassium hydroxide solution/toluene or methylene chloride), with addition of 0.01 to 1 mol of a phase transfer catalyst (such as ammonium or phosphonium compounds), the alcoholates being reacted with the halides present in the organic phase in the organic phase or at the phase boundary.

The following acids can preferably be used for the preparation of physiologically acceptable acid addition salts of the compounds of the formula (I): the hydrogen halide acids, (such as hydrobromic acid and, especially, hydrochloric acid), phosphoric acid, nitric acid, sulphuric acid, monofunctional and bifunctional carboxylic acids and hydroxycarboxylic acids, (such as acetic acid, maleic acid, succinic acid, fumaric acid, tartaric acid, citric acid, salicyclic acid, sorbic acid and lactic acid) and sulphonic acids (such as, for example, p-toluenesulphonic acid and 1,5-napthalenedisulphonic acid).

The acid solution salts of the compounds of the formula (I) can be obtained in a simple manner by customary salt formation methods, for example by dissolving a compound of the formula (I) in a suitable inert solvent and adding the acid (for example hydrochloric acid), and can be isolated in a known manner, for example by filtration, and, if appropriate, purified by washing with an inert organic solvent.

Salts of metals of main groups II to IV and subgroups I to II and IV to VIII can preferably be used for the preparation of metal salt complexes of the compounds of the formula (I), copper, zinc, manganese, magnesium, tin, iron and nickel being mentioned as examples. Possible anions of the salts are those which, preferably, are derived from the following acids: hydrogen halide acids (such as hydrochloric acid and hydrobromic acid), and furthermore phosphoric acid, nitric acid and sulphuric acid.

The metal salt complexes of compounds of the formula (I) can be obtained by customary processes in a simple manner, thus, for example, by dissolving the metal salt in alcohol, for example ethanol, and adding the solution to the compounds of the formula (I). The metal salt complexes can be isolated in a known manner, for example by filtration, and, if appropriate, purified by recrystallization.

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at borders, at airports or in fruit orchards. The inhibition of growth of herbaceous and woody plants at borders and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus, it is possible, for example, to increase the content of sugar in sugar beet, sugar cane, pineapples and citrus fruit or to increase the protein content in soy beans or cereals. Using growth regulators it is also possible, for example, to inhibit the degradation of desired constituents, such as sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants and also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cottom, but is also of interest for facilitating harvesting in other crops, such as in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the forces required to detach the fruit at harvest time so as to permit mechnical harvesting or facilitate manual harvesting.

Using growth regulators, it is futhermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out completely mechanical or manual harvesting in only a single pass, for example in the case of tobacco, tomatoes or coffee.

Using growth regulators, it is furthermore possible to influence the latent period of seeds or buds of plants, so that the plants, such as pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds used according to the invention can be used with particularly good success for combating those fungi which cause powdery mildew diseases; thus, for combating Erysiphe species for example, against the powdery mildew of barley or cereal causative organism (Erysiphe graminis), Podosphaera species, for example against the powdery mildew of apple causative organism (Podosphaera Leucotricha), and Sphaerotheca species, for example against the powdery mildew of cucumber causative organism (Sphaerotheca fuligenea), and also for combating Puccinia species, for example, against the brown rust of wheat causative organism (Puccinia recondita). It should be noted that the substances according to the invention also display a broad fungicidal in vitro action.

When used in appropriate amounts, the active compounds according to the invention also exhibit herbicidal properties.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic ior alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earch, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions foams, suspensions, wettable powders, pastes, soluble powders, dusting agents and granules. They are used in the customary manner, for example by watering, spraying, atomizing, scattering, dusting, foaming or coating. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amounts applied can be varied within a substantial range. In general, 0.01 to 50 kg, preferably 0.05 to 10 kg, of active compound are used per hectare of soil surface.

When the substances according to the invention are used as fungicides, the amount applied can also be varied within a substantial range, depending on the mode of application.

Thus, especially in the treatment of parts of plants, the active compound concentrations in the use forms are generally between 1 and 0.0001% by weight, preferably between 0.5 and 0.001%.

In the treatment of seed, active compound amounts of 0.001 to 50 g, preferably 0.01 to 10 g, per kilogram of seed are generally required.

In the treatment of soil, active compound concentrations of 0.00001 to 0.1% by weight, preferably of 0.0001 to 0.02%, are generally required at the place of action.

The present invention also provides plant growth regulating or fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

Preparative Example

Example 1

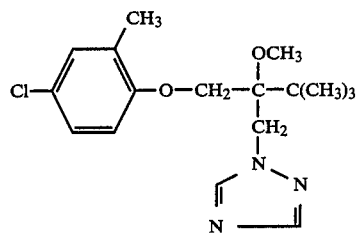

27 g (0.9 mol) of 80% strength sodium hydride were introduced in portions into a solution of 290 g (0.86 mol) of 2-(4-chloro-2-methyl-phenoxy-methyl)-3,3-dimethyl-1-(1,2,4-triazol-1-yl)-2-butanol in 1,600 ml of absolute dioxane at room temperature. The mixture was subsequently stirred at room temperature for 4 hours, and 141.9 g (1 mol) of iodomethane were then added dropwise. The reaction mixture was stirred at 40° C. for 12 hours and another 10 g (0.33 mol) of 80% strength sodium hydride were then added in portions. After the mixture had been stirred at room temperature for three hours, 57 g (0.4 mol) of iodomethane were added and the reaction mixture was subsequently stirred at room temperature for 72 hours. The suspension was filtered, the filtrate was concentrated, the oily residue was taken up in methylene chloride and the methylene chloride mixture was washed twice with water, dried over sodium sulphate and concentrated. 1,5-Naphthalenedisulphonic acid was added to the residue, in acetone, the salt which precipitated was filtered off with suction, washed with acetone and suspended in methylene chloride, and saturated sodium bicarbonate solution was added. The organic phase was separated off, washed and concentrated. 155 g (54% of theory) of 2-(4-chloro-2-methyl-phenoxymethyl)-3,3-dimethyl-2-methoxy-1-(1,2,4-triazol-1-yl)butane were obtained as a light yellow oil of refractive index $n_D^{20} = 1.5390$.

The following compounds of the general formula

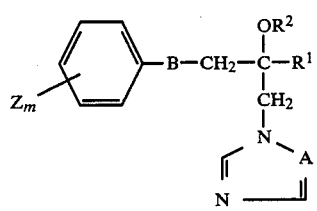

were obtained in an analogous manner and by a process corresponding to that according to the invention:

TABLE 2

| Compound No. | $Z_m$ | B | A | $R^1$ | $R^2$ | Melting point (°C.) or $n_D^{20}$ |
|---|---|---|---|---|---|---|
| 2 | 4-Cl | O | N | C(CH₃)₃ | CH₃ | 198–203 (× HCl) |
| 3 | 2,4-Cl₂ | O | N | C(CH₃)₃ | CH₃ | 1.5382 |
| 4 | 4-Cl | CH₂ | N | C(CH₃)₃ | CH₃ | 1.5354 |
| 5 | 4-F | CH₂ | N | C(CH₃)₃ | CH₃ | 1.5212 |

The plant growth regulating and fungicidal activity of the compounds of this invention is illustrated by the following biotest examples.

In these examples, the compounds according to the present invention are each identified by the number (given in brackets) from Example 1 and Table 2.

The known comparison compounds are identified as follows:

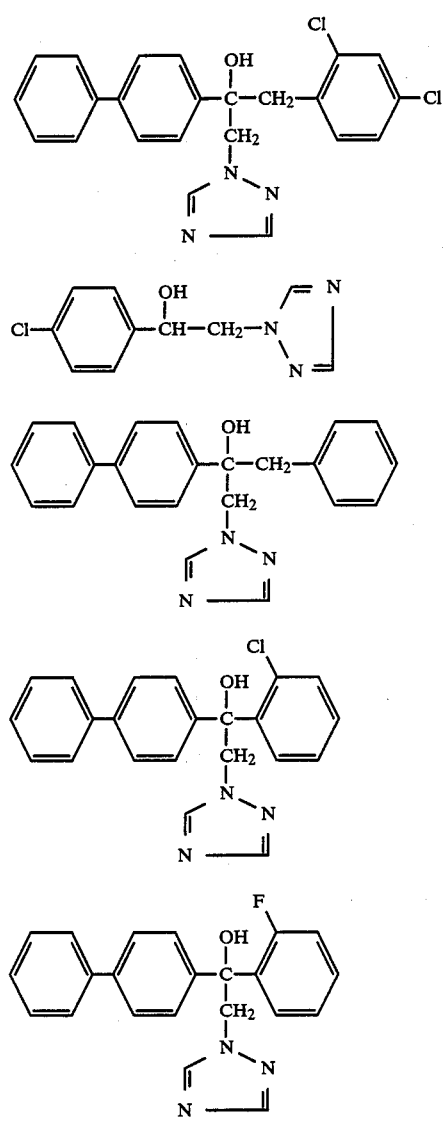

Example A

Sphaerotheca test (cucumber)/protective

Solvent: 0.7 parts by weight of acetone
Emulsifier: 0.3 parts by weight of alkylaryl polyglycol ether.

To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were dusted with conidia of the fungus *Sphaerotheca fuliginea*.

The plants were then placed in a greenhouse at 23° to 24° C. and at a relative atmospheric humidity of about 75%.

Evaluation was carried out 10 days after the inoculation.

In this test, a clearly superior activity compared with the prior art was shown, for example, by the compounds: (1), (3) and (4).

Example B

Podosphaera test (apple)/protective

Solvent: 4.7 parts by weight of acetone
Emulsifier: 0.3 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated by dusting with conidia of the powdery mildew of apple causative organism (*Podosphaera leucotricha*).

The plants were then placed in a greenhouse at 23° C. and a relative atmospheric humidity of about 70%.

Evaluation was carried out 9 days after the inoculation.

In this test, a clearly superior activity compared with the prior art was shown, for example, by the compounds: (1), (2), (3) and (4).

Example C

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis f.* sp. *hordei*.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (2), (1), (3) and (4).

Example D

Puccinia test (wheat)/protective

Solvent: 100 parts by weight of dimethylformamide
Emulsifier: 0.25 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were inoculated with a spore suspension of *Puccinia recondita* in 0.1% strength aqueous agar solution. After the spore suspension had dried on, the plants were sprayed with the preparation of active compound until dew-moist. The plants remained in an incubation cabin at 20° C. and 100% relative atmospheric humidity for 24 hours.

The plants were placed in a greenhouse at a temperature of about 20° C. and a relative atmospheric humidity of about 80% in order to promote the development of rust pustules.

Evaluation was carried out 10 days after the inoculation.

In this test, a clearly superior activity compared with the prior art was shown, for example, by the compounds (2), (1), (3) and (4).

Example E

Erysiphe test (barley)/seed treatment

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of *Erysiphe graminis f.* sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compounds (2), (1), (3) and (4).

Example F

Influence on growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of the plants was measured and the influence on growth in percent of the additional growth of the control plants was calculated. 0% infuence on growth denoted a growth which corresponded to that of the control plants. Negative values characterized an inhibition of growth in comparison to the control plants, while positive values characterized a promotion of growth in comparison to the control plants.

In this test, active compounds (2), (1), (3) and (4), exhibited a more powerful influence on growth than the compounds (B), (D) and (E) known from the prior art.

Example G

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were frown in a greenhouse until the 5th secondary leaf had unfolded completely. In this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

In this test, active compounds (2), (3) and (1) exhibited a better inhibition of growth than the compounds (B), (D) and (E) known from the prior art.

Example H

Inhibition of growth of soy beans

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

In this test, the active compounds (2), (1), (3) and (4) exhibited a more powerful inhibition of growth than compounds (A), (B) and (D) known from the prior art.

It will be appreciated that the instant specification and examples are set forth by way of illustration and not limitation, and that various modifications and changes may be made without departing from the spirit and scope of the present invention.

We claim:

1. An ether derivative of a substituted 1-hydroxyalkylazole of the formula

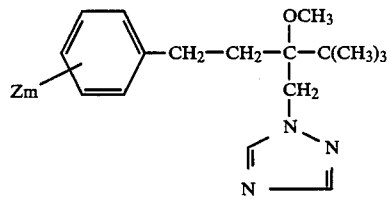

in which

Z is fluorine or chlorine and m is 0 or 1 or an addition product thereof with an acid or metal salt.

2. A compound according to claim 1, wherein such compound 2,2-dimethyl-3-(1,2,4-triazol-1-yl-methyl)-3-methoxy-5-(4-chlorophenyl)-pentane of the formula

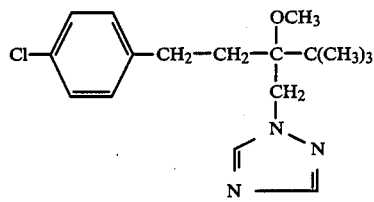

or an addition product thereof.

3. A compound according to claim 1, wherein such compound is 2,2-dimethyl-3-(1,2,4-triazol-1-yl-methyl)-3-methoxy-5-(4-fluoro-phenyl)-pentane of the formula

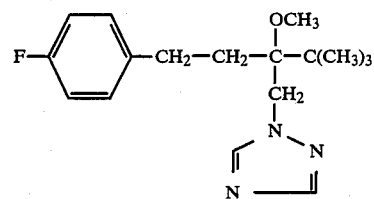

or an addition product thereof.

4. A fungicidal composition, comprising a fungicidally effective amount of a compound or addition product according to claim 1 in admixture with a diluent.

5. A method of combating fungi comprising applying to the fungi, or to a habitat thereof, a fungicidally effective amount of a compound or addition product according to claim 1.

6. A method of combating fungi comprising applying to the fungi, or to a habitat thereof, a fungicidally effective amount of a compound or addition product according to claim 2.

7. A method of combating fungi comprising applying to the fungi, or to a habitat thereof, a fungicidally effective amount of a compound or addition product according to claim 3.

* * * * *